United States Patent [19]
Ohba et al.

[11] Patent Number: 5,747,450
[45] Date of Patent: May 5, 1998

[54] MICROORGANISM AND INSECTICIDE

[75] Inventors: Michio Ohba, Fukuoka; Hidenori Iwahana; Ryoichi Sato, both of Tokyo; Nobukazu Suzuki, Ibaraki; Katsutoshi Ogiwara, Ibaraki; Kazunobu Sakanaka, Ibaraki; Hidetaka Hori, Kanagawa; Shouji Asano; Tadaaki Kawasugi, both of Ibaraki, all of Japan

[73] Assignee: Kubota Corporation, Ibaraki, Japan

[21] Appl. No.: 272,887

[22] Filed: Jul. 8, 1994

Related U.S. Application Data

[62] Division of Ser. No. 915,203, Jul. 23, 1992, Pat. No. 5,359,048.

[30] Foreign Application Priority Data

Aug. 2, 1991 [JP] Japan .................................. 3-193810

[51] Int. Cl.$^6$ .................................................. C07K 14/325
[52] U.S. Cl. ............................ 514/12; 435/69.1; 435/71.3
[58] Field of Search ........................ 514/12; 536/23.71; 800/205; 435/69.1, 252.1, 71.3; 424/93.461

[56] References Cited

U.S. PATENT DOCUMENTS 4,966,765  10/1990  Payne et al. ........................ 435/252.5

FOREIGN PATENT DOCUMENTS

| 2365188 | 8/1992 | Australia . |
| 7752691 | 8/1993 | Australia . |
| 0202739 | 11/1985 | European Pat. Off. . |
| 0337604 | 10/1989 | European Pat. Off. . |
| 0382990 | 8/1990 | European Pat. Off. . |
| 8901515 | 2/1989 | WIPO . |

OTHER PUBLICATIONS

Couch, T.L. (1980) "Mosquito Pathogenicity of *Bacillus thuringiensis* var. *israelensis*" Developments in Industrial Microbiology 22:61–76.

Beegle, C.C. (1978) "Use of Entomogenous Bacteria in Agroecosystems" Developments in Industrial Microbiology 20:97–104.

Krieg, V.A. et al. (1983) "*Bacillus thuringiensis* var. *tenebrionis*: ein neuer, gegenuber Larven von Coleopteran wirksamer Pathotyp" Z. ang. Ent. 96:500–508.

Boswell et al. in Computational Molecular Biology Sources and Methods for Sequence Analysis (Lesk, ed.) Oxford University Press, Oxford, 1988, pp. 170–171.

*Primary Examiner*—Che S. Chereskin
*Attorney, Agent, or Firm*—Saliwanchik, Lloyd & Saliwanchik

[57] ABSTRACT

*Bacillus thuringiensis* serovar *japonensis* strain Buibui (FERM BP-3465) belonging to *Bacillus thuringiensis* serovar *japonensis* and capable of producing insecticidal toxin proteins to kill coleopterous larvae, and an insecticide containing, as an effective ingredient, the toxin proteins produced.

2 Claims, 8 Drawing Sheets

SEQUENCE LISTING

```
( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
                ( A ) LENGTH: 3797 base pairs
                ( B ) TYPE: nucleic acid
                ( C ) STRANDEDNESS: single
                ( D ) TOPOLOGY: linear ( i i ) MOLECULE TYPE: DNA (genomic)

( v i ) ORIGINAL SOURCE:
                ( A ) ORGANISM: Bacillus thuringiensis
                ( B ) STRAIN: japonensis
                ( C ) INDIVIDUAL ISOLATE: Buibui ( i x ) FEATURE:
                ( A ) NAME/KEY: CDS
                ( B ) LOCATION: 187..3636

( x i ) SEQUENCE DESCRIPTION: SEQ ID NO:1:

AATTCTAATG ACACAGTAGA ATATTTTTAA AATAAAGATG GAAGGGGGAA TATGAAAAAA      60

ATATAATCAT AAGAGTCATA CAAAAAGATT GTATGTTAAA ACAAAAAAAT CCTGTAGGAA     120

TAGGGGTTTA AAAGCAATCA TTTGAAAAGA TAGTTATATT AAATTGTATG TATAGGGGGA     180

AAAAAG ATG AGT CCA AAT AAT CAA AAT GAG TAT GAA ATT ATA GAT GCT        228
       Met Ser Pro Asn Asn Gln Asn Glu Tyr Glu Ile Ile Asp Ala
         1               5                  10

TTA TCA CCC ACT TCT GTA TCC GAT AAT TCT ATT AGA TAT CCT TTA GCA       276
Leu Ser Pro Thr Ser Val Ser Asp Asn Ser Ile Arg Tyr Pro Leu Ala
 15                  20                  25                  30

AAC GAT CAA ACG AAC ACA TTA CAA AAC ATG AAT TAT AAA GAT TAT CTG       324
Asn Asp Gln Thr Asn Thr Leu Gln Asn Met Asn Tyr Lys Asp Tyr Leu
                 35                  40                  45

AAA ATG ACC GAA TCA ACA AAT GCT GAA TTG TCT CGA AAT CCC GGG ACA       372
Lys Met Thr Glu Ser Thr Asn Ala Glu Leu Ser Arg Asn Pro Gly Thr
             50                  55                  60

TTT ATT AGT GCG CAG GAT GCG GTT GGA ACT GGA ATT GAT ATT GTT AGT       420
Phe Ile Ser Ala Gln Asp Ala Val Gly Thr Gly Ile Asp Ile Val Ser
         65                  70                  75

ACT ATA ATA AGT GGT TTA GGG ATT CCA GTG CTT GGG GAA GTC TTC TCA       468
Thr Ile Ile Ser Gly Leu Gly Ile Pro Val Leu Gly Glu Val Phe Ser
     80                  85                  90

ATT CTG GGT TCA TTA ATT GGC TTA TTG TGG CCG TCA AAT AAT GAA AAT       516
Ile Leu Gly Ser Leu Ile Gly Leu Leu Trp Pro Ser Asn Asn Glu Asn
 95                 100                 105                 110

GTA TGG CAA ATA TTT ATG AAT CGA GTG GAA GAG CTA ATT GAT CAA AAA       564
Val Trp Gln Ile Phe Met Asn Arg Val Glu Glu Leu Ile Asp Gln Lys
                115                 120                 125

ATA TTA GAT TCT GTA AGA TCA AGA GCC ATT GCA GAT TTA GCT AAT TCT       612
Ile Leu Asp Ser Val Arg Ser Arg Ala Ile Ala Asp Leu Ala Asn Ser
            130                 135                 140

AGA ATA GCT GTA GAG TAC TAT CAA AAT GCA CTT GAA GAC TGG AGA AAA       660
Arg Ile Ala Val Glu Tyr Tyr Gln Asn Ala Leu Glu Asp Trp Arg Lys
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 145 |     |     |     |     |     | 150 |     |     |     |     |     | 155 |     |      |
| AAC | CCA | CAC | AGT | ACA | CGA | AGC | GCA | GCA | CTT | GTA | AAG | GAA | AGA | TTT | GGA | 708  |
| Asn | Pro | His | Ser | Thr | Arg | Ser | Ala | Ala | Leu | Val | Lys | Glu | Arg | Phe | Gly |      |
|     | 160 |     |     |     |     | 165 |     |     |     |     | 170 |     |     |     |     |      |
| AAT | GCA | GAA | GCA | ATT | TTA | CGT | ACT | AAC | ATG | GGT | TCA | TTT | TCT | CAA | ACG | 756  |
| Asn | Ala | Glu | Ala | Ile | Leu | Arg | Thr | Asn | Met | Gly | Ser | Phe | Ser | Gln | Thr |      |
| 175 |     |     |     | 180 |     |     |     |     | 185 |     |     |     |     | 190 |     |      |
| AAT | TAT | GAG | ACT | CCA | CTC | TTA | CCC | ACA | TAT | GCA | CAG | GCC | GCC | TCT | CTG | 804  |
| Asn | Tyr | Glu | Thr | Pro | Leu | Leu | Pro | Thr | Tyr | Ala | Gln | Ala | Ala | Ser | Leu |      |
|     |     |     |     | 195 |     |     |     | 200 |     |     |     |     | 205 |     |     |      |
| CAT | TTG | CTT | GTA | ATG | AGG | GAT | GTT | CAA | ATT | TAC | GGG | AAG | GAA | TGG | GGA | 852  |
| His | Leu | Leu | Val | Met | Arg | Asp | Val | Gln | Ile | Tyr | Gly | Lys | Glu | Trp | Gly |      |
|     |     |     | 210 |     |     |     |     | 215 |     |     |     |     | 220 |     |     |      |
| TAT | CCT | CAA | AAT | GAT | ATT | GAC | CTA | TTT | TAT | AAA | GAA | CAA | GTA | TCT | TAT | 900  |
| Tyr | Pro | Gln | Asn | Asp | Ile | Asp | Leu | Phe | Tyr | Lys | Glu | Gln | Val | Ser | Tyr |      |
|     |     | 225 |     |     |     |     | 230 |     |     |     |     | 235 |     |     |     |      |
| ACG | GCT | AGA | TAT | TCC | GAT | CAT | TGC | GTC | CAA | TGG | TAC | AAT | GCT | GGT | TTA | 948  |
| Thr | Ala | Arg | Tyr | Ser | Asp | His | Cys | Val | Gln | Trp | Tyr | Asn | Ala | Gly | Leu |      |
| 240 |     |     |     |     | 245 |     |     |     |     | 250 |     |     |     |     |     |      |
| AAT | AAA | TTA | AGA | GGA | ACG | GGT | GCT | AAG | CAA | TGG | GTG | GAT | TAT | AAT | CGT | 996  |
| Asn | Lys | Leu | Arg | Gly | Thr | Gly | Ala | Lys | Gln | Trp | Val | Asp | Tyr | Asn | Arg |      |
| 255 |     |     |     |     | 260 |     |     |     |     | 265 |     |     |     |     | 270 |      |
| TTC | CGA | AGA | GAA | ATG | AAT | GTG | ATG | GTA | TTG | GAT | CTA | GTT | GCA | TTA | TTT | 1044 |
| Phe | Arg | Arg | Glu | Met | Asn | Val | Met | Val | Leu | Asp | Leu | Val | Ala | Leu | Phe |      |
|     |     |     |     | 275 |     |     |     |     | 280 |     |     |     |     | 285 |     |      |
| CCA | AAC | TAC | GAT | GCG | CGT | ATA | TAT | CCA | CTG | GAA | ACA | AAT | GCA | GAA | CTT | 1092 |
| Pro | Asn | Tyr | Asp | Ala | Arg | Ile | Tyr | Pro | Leu | Glu | Thr | Asn | Ala | Glu | Leu |      |
|     |     |     | 290 |     |     |     |     | 295 |     |     |     |     | 300 |     |     |      |
| ACA | AGA | GAA | ATT | TTC | ACA | GAT | CCT | GTT | GGA | AGT | TAC | GTA | ACT | GGA | CAA | 1140 |
| Thr | Arg | Glu | Ile | Phe | Thr | Asp | Pro | Val | Gly | Ser | Tyr | Val | Thr | Gly | Gln |      |
|     |     | 305 |     |     |     |     | 310 |     |     |     |     | 315 |     |     |     |      |
| TCG | AGT | ACC | CTT | ATA | TCT | TGG | TAC | GAT | ATG | ATT | CCA | GCA | GCT | CTT | CCT | 1188 |
| Ser | Ser | Thr | Leu | Ile | Ser | Trp | Tyr | Asp | Met | Ile | Pro | Ala | Ala | Leu | Pro |      |
| 320 |     |     |     |     | 325 |     |     |     |     | 330 |     |     |     |     |     |      |
| TCA | TTT | TCA | ACG | CTC | GAG | AAC | CTA | CTT | AGA | AAA | CCT | GAT | TTC | TTT | ACT | 1236 |
| Ser | Phe | Ser | Thr | Leu | Glu | Asn | Leu | Leu | Arg | Lys | Pro | Asp | Phe | Phe | Thr |      |
| 335 |     |     |     |     | 340 |     |     |     |     | 345 |     |     |     |     | 350 |      |
| TTG | CTG | CAA | GAA | ATT | AGA | ATG | TAT | ACA | AGT | TTT | AGA | CAA | AAC | GGT | ACG | 1284 |
| Leu | Leu | Gln | Glu | Ile | Arg | Met | Tyr | Thr | Ser | Phe | Arg | Gln | Asn | Gly | Thr |      |
|     |     |     |     | 355 |     |     |     |     | 360 |     |     |     |     | 365 |     |      |
| ATT | GAA | TAT | TAT | AAT | TAT | TGG | GGA | GGA | CAA | AGG | TTA | ACC | CTT | TCT | TAT | 1332 |
| Ile | Glu | Tyr | Tyr | Asn | Tyr | Trp | Gly | Gly | Gln | Arg | Leu | Thr | Leu | Ser | Tyr |      |
|     |     |     | 370 |     |     |     |     | 375 |     |     |     |     | 380 |     |     |      |
| ATC | TAT | GGT | TCC | TCA | TTC | AAT | AAA | TAT | AGT | GGG | GTT | CTT | GCC | GGT | GCT | 1380 |
| Ile | Tyr | Gly | Ser | Ser | Phe | Asn | Lys | Tyr | Ser | Gly | Val | Leu | Ala | Gly | Ala |      |
|     |     | 385 |     |     |     |     | 390 |     |     |     |     | 395 |     |     |     |      |
| GAG | GAT | ATT | ATT | CCT | GTG | GGT | CAA | AAT | GAT | ATT | TAC | AGA | GTT | GTA | TGG | 1428 |
| Glu | Asp | Ile | Ile | Pro | Val | Gly | Gln | Asn | Asp | Ile | Tyr | Arg | Val | Val | Trp |      |
| 400 |     |     |     |     | 405 |     |     |     |     | 410 |     |     |     |     |     |      |
| ACT | TAT | ATA | GGA | AGG | TAC | ACG | AAT | AGT | CTG | CTA | GGA | GTA | AAT | CCA | GTT | 1476 |
| Thr | Tyr | Ile | Gly | Arg | Tyr | Thr | Asn | Ser | Leu | Leu | Gly | Val | Asn | Pro | Val |      |
| 415 |     |     |     |     | 420 |     |     |     |     | 425 |     |     |     |     | 430 |      |
| ACT | TTT | TAC | TTC | AGT | AAT | AAT | ACA | CAA | AAA | ACT | TAT | TCG | AAG | CCA | AAA | 1524 |
| Thr | Phe | Tyr | Phe | Ser | Asn | Asn | Thr | Gln | Lys | Thr | Tyr | Ser | Lys | Pro | Lys |      |
|     |     |     |     | 435 |     |     |     |     | 440 |     |     |     |     | 445 |     |      |
| CAA | TTC | GCG | GGT | GGA | ATA | AAA | ACA | ATT | GAT | TCC | GGC | GAA | GAA | TTA | ACT | 1572 |
| Gln | Phe | Ala | Gly | Gly | Ile | Lys | Thr | Ile | Asp | Ser | Gly | Glu | Glu | Leu | Thr |      |
|     |     |     | 450 |     |     |     |     | 455 |     |     |     |     | 460 |     |     |      |
| TAC | GAA | AAT | TAT | CAA | TCT | TAT | AGT | CAC | AGG | GTA | AGT | TAC | ATT | ACA | TCT | 1620 |
| Tyr | Glu | Asn | Tyr | Gln | Ser | Tyr | Ser | His | Arg | Val | Ser | Tyr | Ile | Thr | Ser |      |

```
        465                    470                       475
TTT GAA ATA AAA AGT ACC GGT GGT ACA GTA TTA GGA GTA GTT CCT ATA          1668
Phe Glu Ile Lys Ser Thr Gly Gly Thr Val Leu Gly Val Val Pro Ile
    480             485                 490

TTT GGT TGG ACG CAT AGT AGT GCC AGT CGC AAT AAC TTT ATT TAC GCA          1716
Phe Gly Trp Thr His Ser Ser Ala Ser Arg Asn Asn Phe Ile Tyr Ala
495             500                 505                 510

ACA AAA ATC TCA CAA ATC CCA ATC AAT AAA GCA AGT AGA ACT AGC GGT          1764
Thr Lys Ile Ser Gln Ile Pro Ile Asn Lys Ala Ser Arg Thr Ser Gly
                515                 520                 525

GGA GCG GTT TGG AAT TTC CAA GAA GGT CTA TAT AAT GGA GGA CCT GTA          1812
Gly Ala Val Trp Asn Phe Gln Glu Gly Leu Tyr Asn Gly Gly Pro Val
            530                 535                 540

ATG AAA TTA TCT GGG TCT GGT TCC CAA GTA ATA AAC TTA AGG GTC GCA          1860
Met Lys Leu Ser Gly Ser Gly Ser Gln Val Ile Asn Leu Arg Val Ala
        545                 550                 555

ACA GAT GCA AAG GGA GCA AGT CAA AGA TAT CGT ATT AGA ATC AGA TAT          1908
Thr Asp Ala Lys Gly Ala Ser Gln Arg Tyr Arg Ile Arg Ile Arg Tyr
    560                 565                 570

GCC TCT GAT AGA GCG GGT AAA TTT ACG ATA TCT TCC AGA TCT CCA GAG          1956
Ala Ser Asp Arg Ala Gly Lys Phe Thr Ile Ser Ser Arg Ser Pro Glu
575                 580                 585                 590

AAT CCT GCA ACC TAT TCA GCT TCT ATT GCT TAT ACA AAT ACT ATG TCT          2004
Asn Pro Ala Thr Tyr Ser Ala Ser Ile Ala Tyr Thr Asn Thr Met Ser
                595                 600                 605

ACA AAT GCT TCT CTA ACG TAT AGT ACT TTT GCA TAT GCA GAA TCT GGC          2052
Thr Asn Ala Ser Leu Thr Tyr Ser Thr Phe Ala Tyr Ala Glu Ser Gly
            610                 615                 620

CCT ATA AAC TTA GGG ATT TCG GGA AGT TCA AGG ACT TTT GAT ATA TCT          2100
Pro Ile Asn Leu Gly Ile Ser Gly Ser Ser Arg Thr Phe Asp Ile Ser
        625                 630                 635

ATT ACA AAA GAA GCA GGT GCT GCT AAC CTT TAT ATT GAT AGA ATT GAA          2148
Ile Thr Lys Glu Ala Gly Ala Ala Asn Leu Tyr Ile Asp Arg Ile Glu
    640                 645                 650

TTT ATT CCA GTT AAT ACG TTA TTT GAA GCA GAA GAA GAC CTA GAT GTG          2196
Phe Ile Pro Val Asn Thr Leu Phe Glu Ala Glu Glu Asp Leu Asp Val
655                 660                 665                 670

GCA AAG AAA GCT GTG AAT GGC TTG TTT ACG AAT GAA AAA GAT GCC TTA          2244
Ala Lys Lys Ala Val Asn Gly Leu Phe Thr Asn Glu Lys Asp Ala Leu
                675                 680                 685

CAG ACA AGT GTA ACG GAT TAT CAA GTC AAT CAA GCG GCA AAC TTA ATA          2292
Gln Thr Ser Val Thr Asp Tyr Gln Val Asn Gln Ala Ala Asn Leu Ile
            690                 695                 700

GAA TGC CTA TCC GAT GAG TTA TAC CCA AAT GAA AAA CGA ATG TTA TGG          2340
Glu Cys Leu Ser Asp Glu Leu Tyr Pro Asn Glu Lys Arg Met Leu Trp
        705                 710                 715

GAT GCA GTG AAA GAG GCG AAA CGA CTT GTT CAG GCA CGT AAC TTA CTC          2388
Asp Ala Val Lys Glu Ala Lys Arg Leu Val Gln Ala Arg Asn Leu Leu
    720                 725                 730

CAA GAT ACA GGC TTT AAT AGG ATT AAT GGA GAA AAC GGA TGG ACG GGA          2436
Gln Asp Thr Gly Phe Asn Arg Ile Asn Gly Glu Asn Gly Trp Thr Gly
735                 740                 745                 750

AGT ACG GGA ATC GAG GTT GTG GAA GGA GAT GTT CTG TTT AAA GAT CGT          2484
Ser Thr Gly Ile Glu Val Val Glu Gly Asp Val Leu Phe Lys Asp Arg
                755                 760                 765

TCG CTT CGT TTG ACA AGT GCG AGA GAG ATT GAT ACA GAA ACA TAT CCA          2532
Ser Leu Arg Leu Thr Ser Ala Arg Glu Ile Asp Thr Glu Thr Tyr Pro
            770                 775                 780

ACG TAT CTC TAT CAA CAA ATA GAT GAA TCG CTT TTA AAA CCA TAT ACA          2580
Thr Tyr Leu Tyr Gln Gln Ile Asp Glu Ser Leu Leu Lys Pro Tyr Thr
```

```
                785                          790                          795
AGA  TAT  AAA  CTA  AAA  GGT  TTT  ATA  GGA  AGT  AGT  CAA  GAT  TTA  GAG  ATT      2628
Arg  Tyr  Lys  Leu  Lys  Gly  Phe  Ile  Gly  Ser  Ser  Gln  Asp  Leu  Glu  Ile
     800                 805                           810

AAA  TTA  ATA  CGT  CAT  CGG  GCA  AAT  CAA  ATC  GTC  AAA  AAT  GTA  CCA  GAT      2676
Lys  Leu  Ile  Arg  His  Arg  Ala  Asn  Gln  Ile  Val  Lys  Asn  Val  Pro  Asp
815                      820                      825                      830

AAT  CTC  TTG  CCA  GAT  GTA  CGC  CCT  GTC  AAT  TCT  TGT  GGT  GGA  GTC  GAT      2724
Asn  Leu  Leu  Pro  Asp  Val  Arg  Pro  Val  Asn  Ser  Cys  Gly  Gly  Val  Asp
                    835                      840                      845

CGC  TGC  AGT  GAA  CAA  CAG  TAT  GTA  GAC  GCG  AAT  TTA  GCA  CTC  GAA  AAC      2772
Arg  Cys  Ser  Glu  Gln  Gln  Tyr  Val  Asp  Ala  Asn  Leu  Ala  Leu  Glu  Asn
               850                      855                      860

AAT  GGA  GAA  AAT  GGA  AAT  ATG  TCT  TCT  GAT  TCC  CAT  GCA  TTT  TCT  TTC      2820
Asn  Gly  Glu  Asn  Gly  Asn  Met  Ser  Ser  Asp  Ser  His  Ala  Phe  Ser  Phe
          865                      870                      875

CAT  ATT  GAT  ACG  GGT  GAA  ATA  GAT  TTG  AAT  GAA  AAT  ACA  GGA  ATT  TGG      2868
His  Ile  Asp  Thr  Gly  Glu  Ile  Asp  Leu  Asn  Glu  Asn  Thr  Gly  Ile  Trp
     880                 885                           890

ATC  GTA  TTT  AAA  ATT  CCG  ACA  ACA  AAT  GGA  AAC  GCA  ACA  CTA  GGA  AAT      2916
Ile  Val  Phe  Lys  Ile  Pro  Thr  Thr  Asn  Gly  Asn  Ala  Thr  Leu  Gly  Asn
895                      900                      905                      910

CTT  GAA  TTT  GTA  GAA  GAG  GGG  CCA  TTG  TCA  GGG  GAA  ACA  TTA  GAA  TGG      2964
Leu  Glu  Phe  Val  Glu  Glu  Gly  Pro  Leu  Ser  Gly  Glu  Thr  Leu  Glu  Trp
                    915                      920                      925

GCC  CAA  CAA  CAA  GAA  CAA  CAA  TGG  CAA  GAC  AAA  ATG  GCA  AGA  AAA  CGT      3012
Ala  Gln  Gln  Gln  Glu  Gln  Gln  Trp  Gln  Asp  Lys  Met  Ala  Arg  Lys  Arg
               930                      935                      940

GCA  GCA  TCA  GAA  AAA  ACA  TAT  TAT  GCA  GCA  AAG  CAA  GCC  ATT  GAT  CGT      3060
Ala  Ala  Ser  Glu  Lys  Thr  Tyr  Tyr  Ala  Ala  Lys  Gln  Ala  Ile  Asp  Arg
          945                      950                      955

TTA  TTC  GCA  GAT  TAT  CAA  GAC  CAA  AAA  CTT  AAT  TCT  GGT  GTA  GAA  ATG      3108
Leu  Phe  Ala  Asp  Tyr  Gln  Asp  Gln  Lys  Leu  Asn  Ser  Gly  Val  Glu  Met
     960                 965                           970

TCA  GAT  TTG  TTG  GCA  GCC  CAA  AAC  CTT  GTA  CAG  TCC  ATT  CCT  TAC  GTA      3156
Ser  Asp  Leu  Leu  Ala  Ala  Gln  Asn  Leu  Val  Gln  Ser  Ile  Pro  Tyr  Val
975                      980                      985                      990

TAT  AAT  GAT  GCG  TTA  CCG  GAA  ATC  CCT  GGA  ATG  AAC  TAT  ACG  AGT  TTT      3204
Tyr  Asn  Asp  Ala  Leu  Pro  Glu  Ile  Pro  Gly  Met  Asn  Tyr  Thr  Ser  Phe
                    995                     1000                     1005

ACA  GAG  TTA  ACA  AAT  AGA  CTC  CAA  CAA  GCA  TGG  AAT  TTG  TAT  GAT  CTT      3252
Thr  Glu  Leu  Thr  Asn  Arg  Leu  Gln  Gln  Ala  Trp  Asn  Leu  Tyr  Asp  Leu
              1010                     1015                     1020

CAA  AAC  GCT  ATA  CCA  AAT  GGA  GAT  TTT  CGA  AAT  GGA  TTA  AGT  AAT  TGG      3300
Gln  Asn  Ala  Ile  Pro  Asn  Gly  Asp  Phe  Arg  Asn  Gly  Leu  Ser  Asn  Trp
         1025                     1030                     1035

AAT  GCA  ACA  TCA  GAT  GTA  AAT  GTG  CAA  CAA  CTA  AGC  GAT  ACA  TCT  GTC      3348
Asn  Ala  Thr  Ser  Asp  Val  Asn  Val  Gln  Gln  Leu  Ser  Asp  Thr  Ser  Val
    1040                     1045                     1050

CTT  GTC  ATT  CCA  AAC  TGG  AAT  TCT  CAA  GTG  TCA  CAA  CAA  TTT  ACA  GTT      3396
Leu  Val  Ile  Pro  Asn  Trp  Asn  Ser  Gln  Val  Ser  Gln  Gln  Phe  Thr  Val
1055                     1060                     1065                     1070

CAA  CCG  AAT  TAT  AGA  TAT  GTG  TTA  CGT  GTC  ACA  GCG  AGA  AAA  GAG  GGA      3444
Gln  Pro  Asn  Tyr  Arg  Tyr  Val  Leu  Arg  Val  Thr  Ala  Arg  Lys  Glu  Gly
                    1075                     1080                     1085

GTA  GGA  GAC  GGA  TAT  GTG  ATC  ATC  CGT  GAT  GGT  GCA  AAT  CAG  ACA  GAA      3492
Val  Gly  Asp  Gly  Tyr  Val  Ile  Ile  Arg  Asp  Gly  Ala  Asn  Gln  Thr  Glu
              1090                     1095                     1100

ACA  CTC  ACA  TTT  AAT  ATA  TGT  GAT  GAT  GAT  ACA  GGT  GTT  TTA  TCT  ACT      3540
Thr  Leu  Thr  Phe  Asn  Ile  Cys  Asp  Asp  Asp  Thr  Gly  Val  Leu  Ser  Thr
```

```
                    1105                              1110                              1115
GAT    CAA    ACT    AGC    TAT    ATC    ACA    AAA    ACA    GTG    GAA    TTC    ACT    CCA    TCT    ACA       3588
Asp    Gln    Thr    Ser    Tyr    Ile    Thr    Lys    Thr    Val    Glu    Phe    Thr    Pro    Ser    Thr
       1120                         1125                         1130

GAG    CAA    GTT    TGG    ATT    GAC    ATG    AGT    GAG
Glu    Gln    Val    Trp    Ile    Asp    Met    Ser    Glu
1135                         1140

ACC    GAA    GTG    TAT    TCA    ACA    TAGAAAGTGT      3643
                                                        Thr    Glu    Val    Tyr    Ser    Thr
                                                                      1145                  1149

AGAACTCGTG    TTAGAAGAAG    AGTAATCATA    GTTTCCTCC    AGATAGAAGG    TTGATCTGGA                                    3703

GGTTTTCTTA    TAGAGAGAGT    ACTATGAATC    AAATGTTTGA    TGAATGCGTT    GCGAGCGGTT                                   3763

TATCTCAAAT    ATCAACGGTA    CAAGGTTTAT    AAAT                                                                    3797
```

( 2 ) INFORMATION FOR SEQ ID NO:2:

( i ) SEQUENCE CHARACTERISTICS:
       ( A ) LENGTH: 1149 amino acids
       ( B ) TYPE: amino acid
       ( D ) TOPOLOGY: linear ( i i ) MOLECULE TYPE: protein ( x i ) SEQUENCE DESCRIPTION: SEQ ID NO:2:

```
Met    Ser    Pro    Asn    Asn    Gln    Asn    Glu    Tyr    Glu    Ile    Ile    Asp    Ala    Leu    Ser
 1                           5                          10                           15

Pro    Thr    Ser    Val    Ser    Asp    Asn    Ser    Ile    Arg    Tyr    Pro    Leu    Ala    Asn    Asp
              20                          25                           30

Gln    Thr    Asn    Thr    Leu    Gln    Asn    Met    Asn    Tyr    Lys    Asp    Tyr    Leu    Lys    Met
              35                          40                           45

Thr    Glu    Ser    Thr    Asn    Ala    Glu    Leu    Ser    Arg    Asn    Pro    Gly    Thr    Phe    Ile
       50                          55                           60

Ser    Ala    Gln    Asp    Ala    Val    Gly    Thr    Gly    Ile    Asp    Ile    Val    Ser    Thr    Ile
65                           70                          75                                          80

Ile    Ser    Gly    Leu    Gly    Ile    Pro    Val    Leu    Gly    Glu    Val    Phe    Ser    Ile    Leu
                     85                          90                                          95

Gly    Ser    Leu    Ile    Gly    Leu    Leu    Trp    Pro    Ser    Asn    Asn    Glu    Asn    Val    Trp
                     100                         105                          110

Gln    Ile    Phe    Met    Asn    Arg    Val    Glu    Glu    Leu    Ile    Asp    Gln    Lys    Ile    Leu
              115                         120                          125

Asp    Ser    Val    Arg    Ser    Arg    Ala    Ile    Ala    Asp    Leu    Ala    Asn    Ser    Arg    Ile
       130                         135                          140

Ala    Val    Glu    Tyr    Tyr    Gln    Asn    Ala    Leu    Glu    Asp    Trp    Arg    Lys    Asn    Pro
145                         150                          155                                        160

His    Ser    Thr    Arg    Ser    Ala    Ala    Leu    Val    Lys    Glu    Arg    Phe    Gly    Asn    Ala
                     165                         170                                        175

Glu    Ala    Ile    Leu    Arg    Thr    Asn    Met    Gly    Ser    Phe    Ser    Gln    Thr    Asn    Tyr
                     180                         185                                        190

Glu    Thr    Pro    Leu    Leu    Pro    Thr    Tyr    Ala    Gln    Ala    Ala    Ser    Leu    His    Leu
              195                         200                          205

Leu    Val    Met    Arg    Asp    Val    Gln    Ile    Tyr    Gly    Lys    Glu    Trp    Gly    Tyr    Pro
       210                         215                          220

Gln    Asn    Asp    Ile    Asp    Leu    Phe    Tyr    Lys    Glu    Gln    Val    Ser    Tyr    Thr    Ala
225                         230                          235                                        240

Arg    Tyr    Ser    Asp    His    Cys    Val    Gln    Trp    Tyr    Asn    Ala    Gly    Leu    Asn    Lys
                     245                         250                                        255
```

| | | | | | | | | | | | | | | |
|---|---|---|---|---|---|---|---|---|---|---|---|---|---|---|
| Leu | Arg | Gly | Thr 260 | Gly | Ala | Lys | Gln 265 | Trp | Val | Asp | Tyr 270 | Asn | Arg | Phe | Arg |
| Arg | Glu | Met 275 | Asn | Val | Met | Val 280 | Leu | Asp | Leu | Val 285 | Ala | Leu | Phe | Pro | Asn |
| Tyr | Asp 290 | Ala | Arg | Ile | Tyr 295 | Pro | Leu | Glu | Thr | Asn 300 | Ala | Glu | Leu | Thr | Arg |
| Glu 305 | Ile | Phe | Thr | Asp 310 | Pro | Val | Gly | Ser | Tyr 315 | Val | Thr | Gly | Gln | Ser 320 | Ser |
| Thr | Leu | Ile | Ser | Trp 325 | Tyr | Asp | Met | Ile | Pro 330 | Ala | Ala | Leu | Pro 335 | Ser | Phe |
| Ser | Thr | Leu | Glu 340 | Asn | Leu | Leu | Arg | Lys 345 | Pro | Asp | Phe | Phe 350 | Thr | Leu | Leu |
| Gln | Glu | Ile 355 | Arg | Met | Tyr | Thr | Ser 360 | Phe | Arg | Gln | Asn | Gly 365 | Thr | Ile | Glu |
| Tyr | Tyr 370 | Asn | Tyr | Trp | Gly 375 | Gly | Gln | Arg | Leu | Thr 380 | Leu | Ser | Tyr | Ile | Tyr |
| Gly 385 | Ser | Ser | Phe | Asn 390 | Lys | Tyr | Ser | Gly | Val 395 | Leu | Ala | Gly | Ala | Glu 400 | Asp |
| Ile | Ile | Pro | Val | Gly 405 | Gln | Asn | Asp | Ile | Tyr 410 | Arg | Val | Val | Trp 415 | Thr | Tyr |
| Ile | Gly | Arg | Tyr 420 | Thr | Asn | Ser | Leu | Leu 425 | Gly | Val | Asn | Pro | Val 430 | Thr | Phe |
| Tyr | Phe | Ser 435 | Asn | Asn | Thr | Gln | Lys 440 | Thr | Tyr | Ser | Lys | Pro 445 | Lys | Gln | Phe |
| Ala | Gly 450 | Gly | Ile | Lys | Thr | Ile 455 | Asp | Ser | Gly | Glu | Glu 460 | Leu | Thr | Tyr | Glu |
| Asn 465 | Tyr | Gln | Ser | Tyr | Ser 470 | His | Arg | Val | Ser | Tyr 475 | Ile | Thr | Ser | Phe | Glu 480 |
| Ile | Lys | Ser | Thr | Gly 485 | Gly | Thr | Val | Leu | Gly 490 | Val | Val | Pro | Ile | Phe 495 | Gly |
| Trp | Thr | His | Ser 500 | Ser | Ala | Ser | Arg | Asn 505 | Asn | Phe | Ile | Tyr | Ala 510 | Thr | Lys |
| Ile | Ser | Gln | Ile 515 | Pro | Ile | Asn | Lys | Ala 520 | Ser | Arg | Thr | Ser 525 | Gly | Gly | Ala |
| Val | Trp | Asn 530 | Phe | Gln | Glu | Gly | Leu 535 | Tyr | Asn | Gly | Gly 540 | Pro | Val | Met | Lys |
| Leu 545 | Ser | Gly | Ser | Gly | Ser 550 | Gln | Val | Ile | Asn | Leu 555 | Arg | Val | Ala | Thr | Asp 560 |
| Ala | Lys | Gly | Ala | Ser 565 | Gln | Arg | Tyr | Arg | Ile 570 | Arg | Ile | Arg | Tyr | Ala 575 | Ser |
| Asp | Arg | Ala | Gly 580 | Lys | Phe | Thr | Ile | Ser 585 | Ser | Arg | Ser | Pro | Glu 590 | Asn | Pro |
| Ala | Thr | Tyr 595 | Ser | Ala | Ser | Ile | Ala 600 | Tyr | Thr | Asn | Thr | Met 605 | Ser | Thr | Asn |
| Ala | Ser | Leu 610 | Thr | Tyr | Ser | Thr | Phe 615 | Ala | Tyr | Ala | Glu | Ser 620 | Gly | Pro | Ile |
| Asn | Leu 625 | Gly | Ile | Ser | Gly | Ser 630 | Ser | Arg | Thr | Phe | Asp 635 | Ile | Ser | Ile | Thr 640 |
| Lys | Glu | Ala | Gly | Ala 645 | Ala | Asn | Leu | Tyr | Ile 650 | Asp | Arg | Ile | Glu | Phe 655 | Ile |
| Pro | Val | Asn | Thr 660 | Leu | Phe | Glu | Ala | Glu 665 | Asp | Leu | Asp | Val 670 | Ala | Lys |
| Lys | Ala | Val 675 | Asn | Gly | Leu | Phe | Thr 680 | Asn | Glu | Lys | Asp | Ala 685 | Leu | Gln | Thr |

| | | | | | | | | | | | | | |
|---|---|---|---|---|---|---|---|---|---|---|---|---|---|
|Ser|Val|Thr|Asp|Tyr|Gln|Val|Asn|Gln|Ala|Ala|Asn|Leu|Ile|Glu|Cys|
| |690| | | |695| | | |700| | | | | | |
|Leu|Ser|Asp|Glu|Leu|Tyr|Pro|Asn|Glu|Lys|Arg|Met|Leu|Trp|Asp|Ala|
|705| | | | |710| | | |715| | | | | |720|
|Val|Lys|Glu|Ala|Lys|Arg|Leu|Val|Gln|Ala|Arg|Asn|Leu|Leu|Gln|Asp|
| | | | |725| | | | |730| | | | |735| |
|Thr|Gly|Phe|Asn|Arg|Ile|Asn|Gly|Asn|Gly|Trp|Thr|Gly|Ser|Thr|
| | | |740| | | | |745| | | |750| | |
|Gly|Ile|Glu|Val|Val|Glu|Gly|Asp|Val|Leu|Phe|Lys|Asp|Arg|Ser|Leu|
| | |755| | | |760| | | |765| | | | | |
|Arg|Leu|Thr|Ser|Ala|Arg|Glu|Ile|Asp|Thr|Glu|Thr|Tyr|Pro|Thr|Tyr|
| |770| | | |775| | | |780| | | | | | |
|Leu|Tyr|Gln|Gln|Ile|Asp|Glu|Ser|Leu|Leu|Lys|Pro|Tyr|Thr|Arg|Tyr|
|785| | | |790| | | | |795| | | | | |800|
|Lys|Leu|Lys|Gly|Phe|Ile|Gly|Ser|Ser|Gln|Asp|Leu|Glu|Ile|Lys|Leu|
| | | |805| | | | |810| | | | |815| | |
|Ile|Arg|His|Arg|Ala|Asn|Gln|Ile|Val|Lys|Asn|Val|Pro|Asp|Asn|Leu|
| | | |820| | | | |825| | | |830| | | |
|Leu|Pro|Asp|Val|Arg|Pro|Val|Asn|Ser|Cys|Gly|Gly|Val|Asp|Arg|Cys|
|835| | | | |840| | | | |845| | | | | |
|Ser|Glu|Gln|Gln|Tyr|Val|Asp|Ala|Asn|Leu|Ala|Leu|Glu|Asn|Asn|Gly|
|850| | | | |855| | | |860| | | | | | |
|Glu|Asn|Gly|Asn|Met|Ser|Ser|Asp|Ser|His|Ala|Phe|Ser|Phe|His|Ile|
|865| | | |870| | | |875| | | | | |880| |
|Asp|Thr|Gly|Glu|Ile|Asp|Leu|Asn|Glu|Asn|Thr|Gly|Ile|Trp|Ile|Val|
| | | |885| | | | |890| | | | |895| | |
|Phe|Lys|Ile|Pro|Thr|Thr|Asn|Gly|Asn|Ala|Thr|Leu|Gly|Asn|Leu|Glu|
| | | |900| | | | |905| | | | |910| | |
|Phe|Val|Glu|Glu|Gly|Pro|Leu|Ser|Gly|Thr|Leu|Glu|Trp|Ala|Gln|
| | |915| | | | |920| | | | |925| | |
|Gln|Gln|Glu|Gln|Gln|Trp|Gln|Asp|Lys|Met|Ala|Arg|Lys|Arg|Ala|Ala|
| |930| | | | |935| | | |940| | | | | |
|Ser|Glu|Lys|Thr|Tyr|Tyr|Ala|Ala|Lys|Gln|Ala|Ile|Asp|Arg|Leu|Phe|
|945| | | | |950| | | |955| | | | | |960|
|Ala|Asp|Tyr|Gln|Asp|Gln|Lys|Leu|Asn|Ser|Gly|Val|Glu|Met|Ser|Asp|
| | | |965| | | | |970| | | | |975| | |
|Leu|Leu|Ala|Ala|Gln|Asn|Leu|Val|Gln|Ser|Ile|Pro|Tyr|Val|Tyr|Asn|
| | |980| | | | |985| | | | |990| | | |
|Asp|Ala|Leu|Pro|Glu|Ile|Pro|Gly|Met|Asn|Tyr|Thr|Ser|Phe|Thr|Glu|
| | |995| | | |1000| | | | |1005| | | | |
|Leu|Thr|Asn|Arg|Leu|Gln|Gln|Ala|Trp|Asn|Leu|Tyr|Asp|Leu|Gln|Asn|
| |1010| | | |1015| | | |1020| | | | | | |
|Ala|Ile|Pro|Asn|Gly|Asp|Phe|Arg|Asn|Gly|Leu|Ser|Asn|Trp|Asn|Ala|
|1025| | | |1030| | | | |1035| | | | |1040| |
|Thr|Ser|Asp|Val|Asn|Val|Gln|Gln|Leu|Ser|Asp|Thr|Ser|Val|Leu|Val|
| | | |1045| | | | |1050| | | | |1055| | |
|Ile|Pro|Asn|Trp|Asn|Ser|Gln|Val|Ser|Gln|Gln|Phe|Thr|Val|Gln|Pro|
| | |1060| | | | |1065| | | | |1070| | | |
|Asn|Tyr|Arg|Tyr|Val|Leu|Arg|Val|Thr|Ala|Arg|Lys|Glu|Gly|Val|Gly|
| |1075| | | | |1080| | | | |1085| | | | |
|Asp|Gly|Tyr|Val|Ile|Ile|Arg|Asp|Gly|Ala|Asn|Gln|Thr|Glu|Thr|Leu|
| |1090| | | | |1095| | | | |1100| | | | |
|Thr|Phe|Asn|Ile|Cys|Asp|Asp|Asp|Thr|Gly|Val|Leu|Ser|Thr|Asp|Gln|

-continued

| 1105 | | | | 1110 | | | | | 1115 | | | | 1120 | |
|---|---|---|---|---|---|---|---|---|---|---|---|---|---|---|
| Thr | Ser | Tyr | Ile | Thr | Lys | Thr | Val | Glu | Phe | Thr | Pro | Ser | Thr | Glu Gln |
| | | | | 1125 | | | | | 1130 | | | | | 1135 |
| Val | Trp | Ile | Asp | Met | Ser | Glu | Thr | Glu | Val | Tyr | Ser | Thr | | |
| | | | | 1140 | | | 1145 | | | | | | | |

MICROORGANISM AND INSECTICIDE

This is a division of application Ser. No. 07/915,203, filed Jul. 23, 1992, now U.S. Pat. No. 5,359,048.

BACKGROUND OF THE INVENTION

1. Field of the Invention

This invention relates to a novel microorganism belonging to *Bacillus thuringiensis* serovar *japonensis*, to an insecticide derived from this novel microorganism, and to DNA coding for the insecticide.

2. Description of the Related Art

The reported activity spectrum of *B.t.* covers insect species within the order Lepidoptera, many of which are major pests in agriculture and forestry. The activity spectrum also includes the insect order Diptera, which includes mosquitos and black flies. See Couch, T. L. (1980) "Mosquito Pathogenicity of *Bacillus thuringiensis* var. *israelensis*," *Developments in Industrial Microbiology* 22:61–76; Beegle, C. C., (1978) "Use of Entomogenous Bacteria in Agroecosystems," *Developments in Industrial Microbiology* 20:97–104. Krieg et al. (1983) *Z. ang. Ent.* 96:500–508, describe a *B.t.* isolate named *Bacillus thuringiensis* var. *tenebrionis*, which is reportedly active against two beetles in the order Coleoptera. These are the Colorado potato beetle, *Leptinotarsa decemlineata*, and *Agelastica alni*.

In European Patent Application 0 202 739 there is disclosed a novel *B.t.* isolate active against Coleoptera. It is known as *B. thuringiensis* var. *san diego* (*B.t.s.d.*). U.S. Pat. No. 4,966,765 discloses the coleopteran-active *Bacillus thuringiensis* isolate *B.t.* PS86B1. European Patent Application 0 337 604 also discloses a novel *B.t.* isolate active against Coleoptera.

Coleopteran-active *B.t.* strains can be used to control foliar-feeding beetles. The Colorado potato beetle (*Leptinotarsa decemlineata*), for example, is susceptible to the delta-endotoxin of *B.t.s.d.* and larvae are killed upon ingesting a sufficient dose of spore/crystal preparation on treated foliage. Strain cells among *Bacillus thuringiensis* serovar *japonensis* are known to produce insecticidal proteins that kill lepidopteran larvae. However, none of the strain cells among *japonensis* are known to produce toxin proteins other than the insecticidal proteins that kill lepidopterous larvae. Thus, no such strain cells have been available for use as an insecticide to kill insects other than lepidopterans. Furthermore, *Bacillus thuringiensis san diego* and *Bacillus thuringiensis tenebrionis* have no insecticidal effect on larvae of *Anomala cuprea* Hope, which are very destructive to firewood, taro, sweet potato, peanut, and the like.

The current inventors have found a new type of microorganism belonging to *Bacillus thuringiensis* serovar *japonensis* that produces insecticidal proteins to kill coleopterous larvae as distinct from lepidopterous larvae.

BRIEF SUMMARY OF THE INVENTION

The subject invention concerns a novel *Bacillus thuringiensis* (*B.t.*) isolate. The novel *B.t.* isolate, known as *Bacillus thuringiensis* serovar *japonensis* strain Buibui (hereinafter referred to as "*B.t.* Buibui"), has been found to be active against coleopteran pests including the Japanese beetle. A novel δ-endotoxin gene of the invention encodes an ≈130 kDa protein. The nucleotide sequence of this gene is shown in SEQ ID NO. 1. The predicted amino acid sequence of the toxin is shown in SEQ ID NO. 2.

The subject invention also includes variants of *B.t.* Buibui which have substantially the same pesticidal properties as *B.t.* Buibui. These variants would include mutants. Procedures for making mutants are well known in the microbiological art. Ultraviolet light and nitrosoguanidine are used extensively toward this end.

Further, the invention also includes the treatment of substantially intact *B.t.* cells, and recombinant cells containing a gene of the invention, to prolong the pesticidal activity when the substantially intact cells are applied to the environment of a target pest. Such treatment can be by chemical or physical means, or a combination of chemical or physical means, so long as the technique does not deleteriously affect the properties of the pesticide, nor diminish the cellular capability in protecting the pesticide. The treated cell acts as a protective coating for the pesticidal toxin. The toxin becomes available to act as such upon ingestion by a target insect.

BRIEF DESCRIPTION OF THE SEQUENCES

Figure 1:
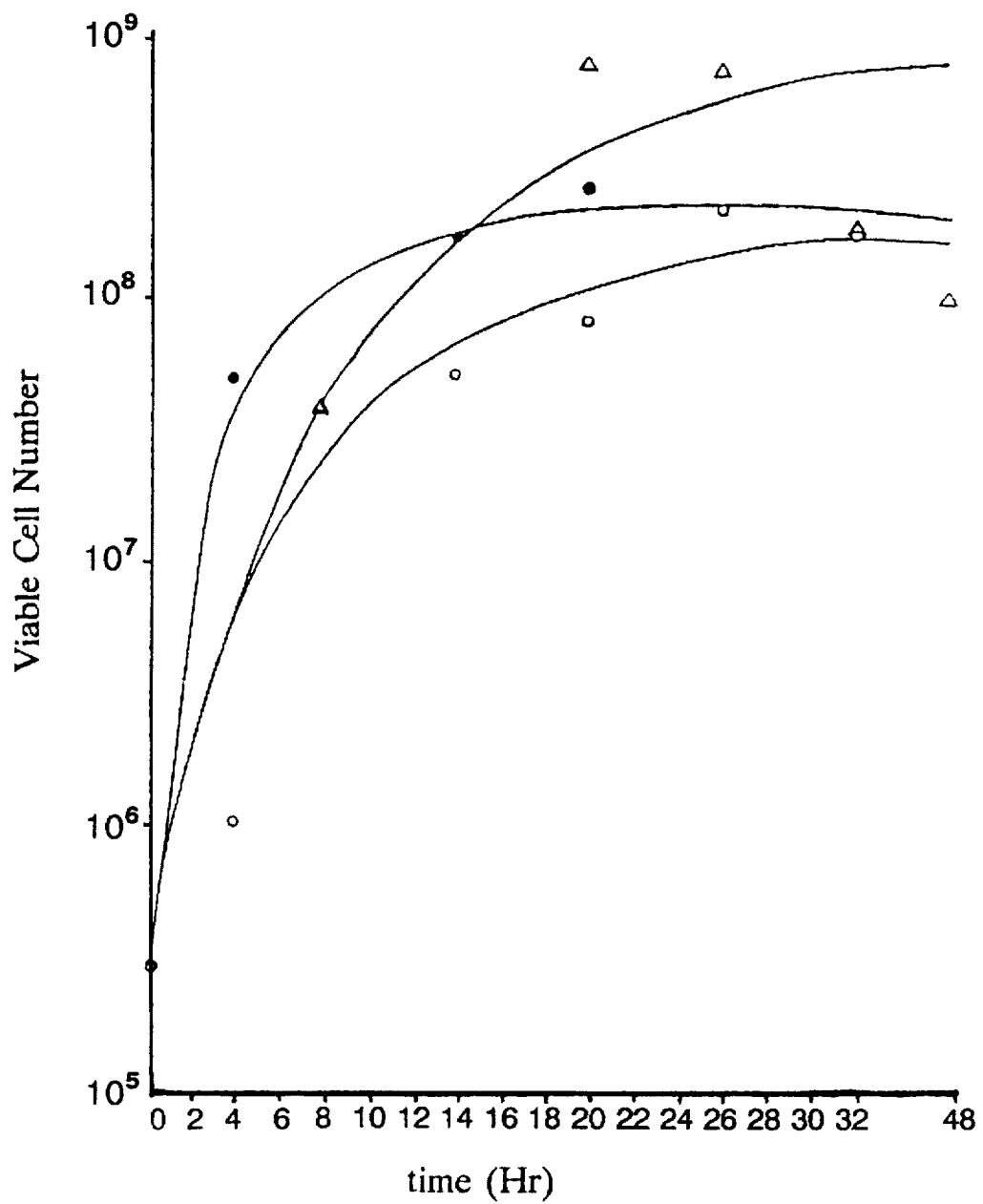
FIG. 1 is a graph showing growth curves of *B.t.* Buibui. The number of colonies produced by splaying the cells in the following agar culture media of the petri dish is measured. -●- LB medium; -○- NB medium; -Δ- NYS medium.

SEQ ID NO. 1 is the composite nucleotide and amino acid sequence of the novel gene of the invention.

SEQ ID NO. 2 is the predicted amino acid sequence of the toxin.

DETAILED DESCRIPTION OF THE INVENTION

The subject invention pertains to a novel strain of *Bacillus thuringiensis* which has the highly advantageous property of expressing at least one endotoxin which is toxic to coleopterans. The novel microorganism has been designated *Bacillus thuringiensis* serovar *japonensis* strain Buibui (hereinafter referred to as "*B.t.* Buibui"). The subject invention further pertains to insecticidal toxin obtainable from *B.t.* Buibui as well as DNA coding for said insecticide. Also disclosed and claimed are microorganisms, other than *Bacillus thuringiensis*, which have been transformed with *B.t.* Buibui DNA so that said transformed microbes express a coleopteran-active toxin. A further aspect of the subject invention is the use of a toxin of the subject invention, or a transformed host-expressing a toxin, to control coleopteran pests. Yet a further aspect of the subject invention pertains to plants transformed with a *B.t.* Buibui DNA coding for toxin active against coleopteran pests.

Novel microorganisms according to the present invention, have been deposited internationally, pursuant to the Treaty of Budapest, with the Fermentation Research Institute, Agency of Industrial Science and Technology, Ministry of International Trade and Industry, which is a recognized international depository organization.

| Culture | Deposit No. | Deposit Date |
| --- | --- | --- |
| *Bacillus thuringiensis* serovar *japonensis* strain Buibui | FERM BP-3465 | June 26, 1992 |
| *Escherichia coli* KBR9207 | FERM BP-3929 | ??? |

The subject cultures have been deposited under conditions that assure that access to the cultures will be available during the pendency of this patent application to one determined by the Commissioner of Patents and Trademarks to be entitled thereto under 37 CFR 1.14 and 35 U.S.C. 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least thirty (30) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

The invention also includes variants of the subject isolates which variants have genes encoding all or part of a toxin of the invention. Such microbial variants may be isolated or they can be made by techniques well known to persons skilled in the art. For example, UV irradiation can be used to prepare variants of host organisms. Likewise, such variants may include asporogenous host cells which also can be prepared by procedures well known in the art. For example, an asporogenous mutant can be obtained through ethylmethane sulfonate (EMS) mutagenesis of a novel isolate. A small percentage of the asporogenous mutants will remain intact and not lyse for extended fermentation periods; these strains are designated lysis minus (−). Lysis minus strains can be identified by screening asporogenous mutants in shake flask media and selecting those mutants that are still intact and contain toxin crystals at the end of the fermentation. Lysis minus strains are suitable for a cell fixation process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30 C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30 C. The resistance to phage is then reconfirmed by plating a lawn of the resistant culture onto a nutrient agar plate. The sensitive strain is also plated in the same manner to serve as the positive control. After drying, a drop of the phage lysate is plated in the center of the plate and allowed to dry. Resistant cultures showed no lysis in the area where the phage lysate has been placed after incubation at 30 C. for 24 hours.

The variants can also be made using ultraviolet light and nitrosoguanidine by procedures well known in the art.

Figure 2:
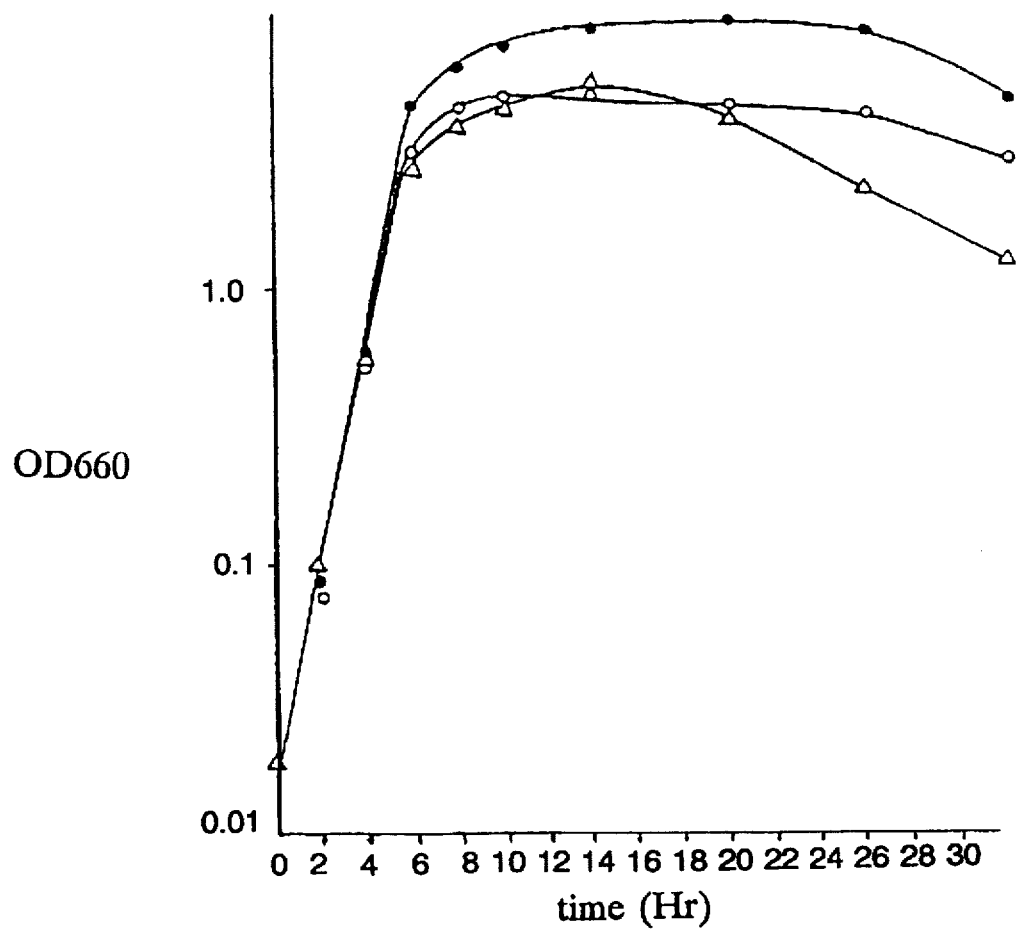
FIG. 2 is a graph showing growth curves of *B.t.* Buibui. The increase of the number of cells is shown by the absorptive increase of media at 660 nm. -●- LB medium; -○- NB medium; -Δ- NYS medium.

The novel microorganism, *B.t.* Buibui, specifically exemplified according to the present invention has the following characteristics:

1. Growth in Different Culture Media. This microorganism may be grown and the toxin proteins may be produced in all types of media that can be used for culturing ordinary bacteria. As shown in FIGS. 1 and 2, the microorganism showed ordinary growth patterns in typical culture media such as NYS, L-broth, and bouillon media. That is, the number of cells began to increase logarithmically after lapse of several hours, and the increase stopped upon lapse of 24 hours. Toxins appeared slightly after the increase in the number of cells. The quantity of toxins, when measured in the main band 130 kDa, was 200 to 300 μg/ml medium.

Figure 3:
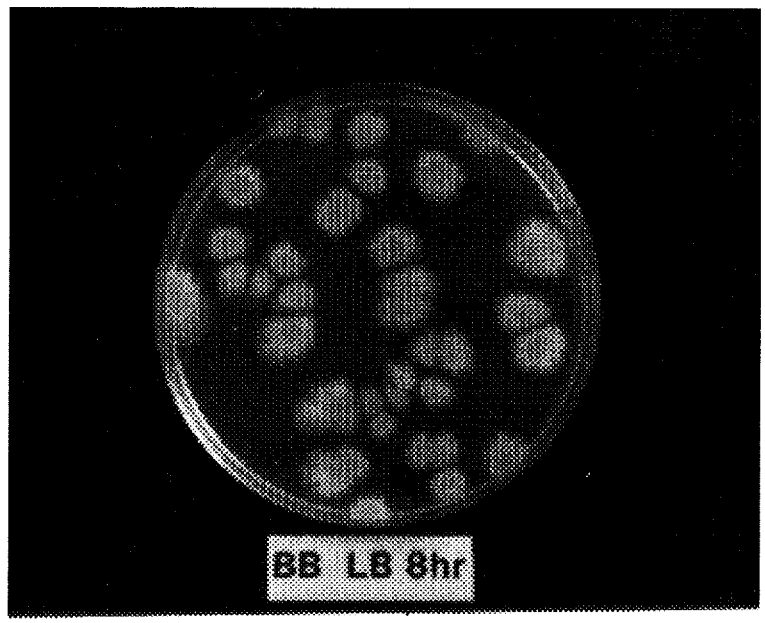
FIG. 3 is a photograph showing colonies of *B.t.* Buibui in LB culture medium. The colonies of Buibui strain were cultured in the LB agar culture media for 72 hours after being cultured in the LB culture media for 8 hours.
Figure 4:
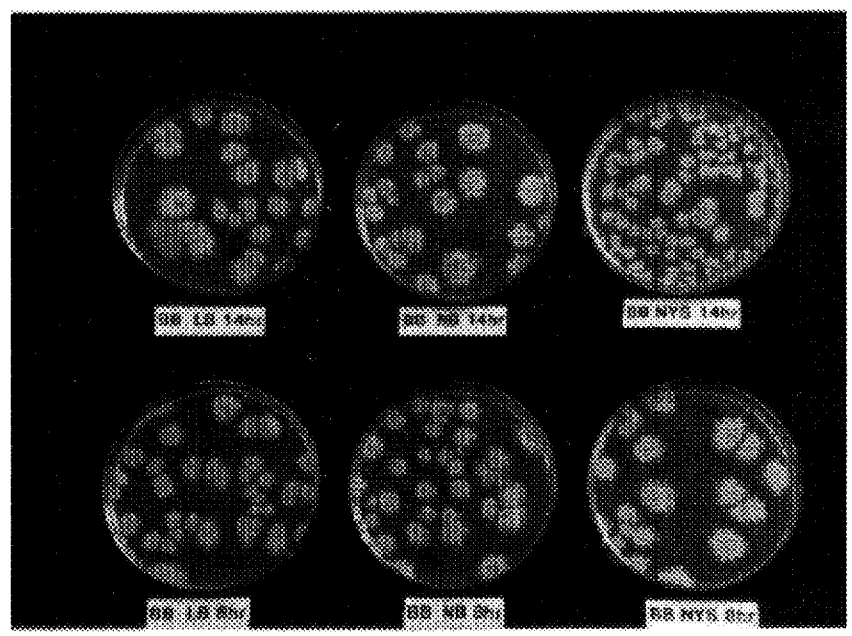
FIG. 4 is a photograph showing colonies of *B.t.* Buibui in various culture media. The colonies of Buibui strain were cultured in the respective agar culture media for 72 hours after being cultured in the LB, NB, and NYS culture media for 8 hours and 14 hours.
Figure 5:
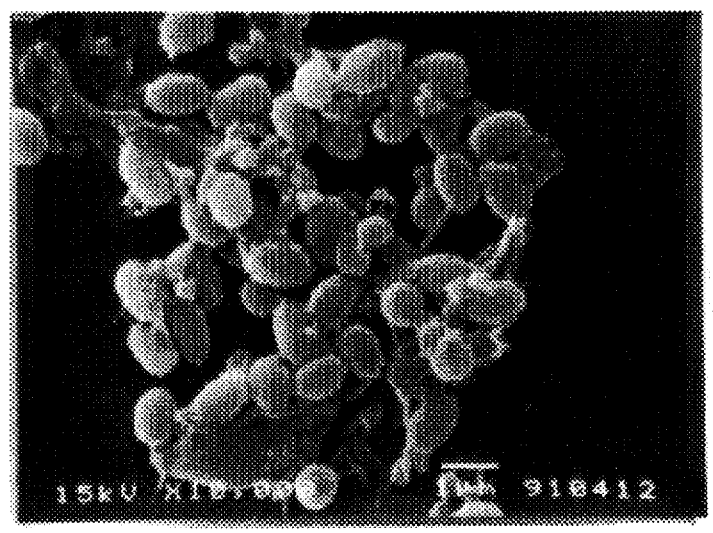
FIG. 5 is a photograph of *japonensis* strain taken with a scanning electron microscope. The dark arrows show crystals of toxin proteins. The elliptic members having wrinkled surfaces are spores.
Figure 6:
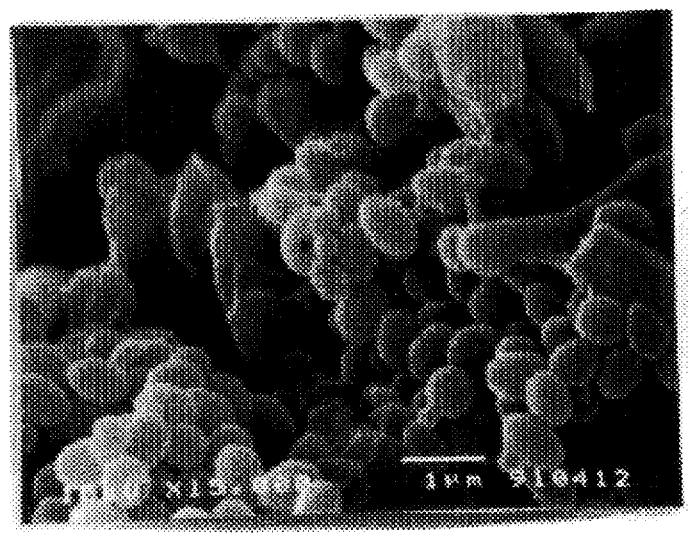
FIG. 6 is a photograph of *B.t.* Buibui taken with the scanning electron microscope. The dark arrows show crystals of toxin proteins. The elliptic members having wrinkled surfaces are spores.
Figure 7:
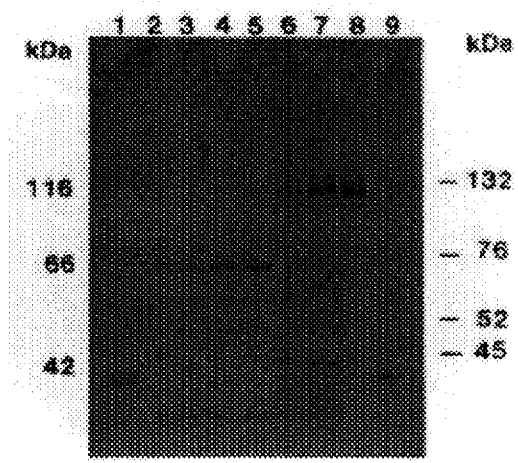
FIG. 7 is a photograph showing sodium dodecyl sulfate polyacrylamide gel electrophoresis. Lane 1 is a molar weight marker. Lane 2 shows toxin proteins produced by *japonensis* strain (5 µl). Lane 3 shows toxin proteins produced by *japonensis* strain (10 µl). Lane 4 shows toxin proteins produced by *japonensis* strain (15 µl). Lane 5 shows toxin proteins produced by *japonensis* strain (20 µl). Lane 6 shows toxin proteins produced by Buibui strain (5 µl). Lane 7 shows toxin proteins produced by Buibui strain (10 µl). Lane 8 shows toxin proteins produced by Buibui strain (5 µl). Lane 9 is a molar weight marker.

2. Morphological Characteristics. As shown in FIGS. 3 and 4, the colonies produced have surface gloss on an agar medium, and spread thinly over the agar surfaces without swelling. Peripheral roughs show characteristics of ordinary *Bacillus* cells. The color of the colonies is light beige.

When observed through a scanning electron microscope, both *Bacillus thuringiensis* serovar *japonensis* and *Bacillus thuringiensis* serovar *japonensis* strain Buibui show spherical crystal proteins. These are distinct from the bipyramid crystals commonly observed with other *B.t.* cells lethal to lepidopterous larvae.

3. Biochemical Appearance. The following tests have been conducted to evaluate the biochemical characteristics of *B.t.* Buibui as compared with conventional *japonensis* strains:

Test 1. Serotyping using antibodies produced against flagellar antigens: This is a method for identifying an unknown organism by employing an antibody active to the proteins of flagella of Bacillus organisms, and utilizing an antigen-antibody reaction in which the flagellar proteins of the unknown organism act as the antigens. Japonensis strain is a subspecies classified and recognized as H23 type (*J. Invertebr. Pathol.* 32:303–309, 1978; *J. Invertebr. Pathol.* 48:129–130, 1986). *B.t.* Buibui is reactive with H-antigen of *japonensis* strain. This property is serologically equivalent to that of *japonensis* strain. Thus, taxonomically, *B.t.* Buibui belongs to the same subspecies as *japonensis* strain. Details of this test are as follows:

(1) Preparation of flagellar H-serum: Forty known types of H-antigen standard strains of *Bacillus thuringiensis* were used. Microorganisms having excellent mobility were selected by using a Craigie tube (0.5% semifluid agar medium), and formalin-killed organisms were prepared. Rabbits were immunized with these organisms. H-serum was prepared by absorbing, from respective antisera, antibodies reactive to *Bacillus thuringiensis* cell antigens. The cell antigens were prepared by heating them to 100 C. and separating the flagella.

(2) Identification of H-antigen: Serum types of H-antigen were identified through agglutination reactions on slide glass (Ohba and Aizawa [1978] *J. Invertebr. Pathol.* 32:303–309). Agglutination values of H-serum were measured through in vitro agglutination reactions (Ohba and Aizawa, supra).

(3) Results: *Japonensis* strain was particularly agglutinated only by the serum for standard strain cells of serovar *japonensis* (H-antigen 23) among standard sera including 40 known types of flagellar antigens only. The agglutination value of *japonensis* H-serum for corresponding homo-antigens was 12,800-fold, and the agglutination value thereof for Buibui strain was 6,400-fold. The agglutination value of *B.t.* Buibui H-serum for homo was 12,800-fold and the agglutination value thereof for *japonensis* standard strain was 6,400-fold. Thus, the two strain cells are determined to be the same species.

Test 2. Insecticidal spectral of crystal proteins produced by *japonensis* strain and *B.t.* Buibui: As shown in Table 1, the insecticidal proteins produced by *B.t.* Buibui showed an insecticidal effect in a concentration of 0.125 to 12.5 μg/ml on *Anomala cuprea* Hope, a coleopteran. However, the insecticidal proteins produced by the *japonensis* strain did not show an insecticidal effect even in a concentration of 100 μg/ml. As shown in Table 2, the insecticidal proteins produced by *japonensis* strain showed a high degree of activity with respect to larvae of lepidopterans such as *Plutella xylostella*, Adoxophyes sp., and *Bombyx mori*. However, the insecticidal proteins produced by *B.t.* Buibui showed little or a very low degree of activity. These results demonstrate that the two strains cannot be said to be the same strains. Furthermore, the observance of coleopteran activity, but no lepidopteran activity is quite surprising and unexpected.

TABLE 1

Insecticidal effects of japonensis strain and B.t. Buibui on *Anomala cuprea* Hope

| Toxin dosage (μg 130 kDa protein/ml) | Death rate* (%) 7th day | 14th day | 22nd day |
|---|---|---|---|
| B.t. Buibui cells | | | |
| 12.5 | 65 | 95 | 95 |
| 1.25 | 45 | 95 | 100 |
| 0.125 | 0 | 30 | 80 |
| Japonensis strain cells | | | |
| 100 | 0 | 0 | 0 |

*Number of samples = 20 larvae in the first instar.

TABLE 2

Insecticidal activities of japonensis strain and Buibui strain with respect to some lepidopterans.

| Samples | Toxin dosage (μg 130 kDa) protein/ml) | Death rates* (%) Buibui | japonensis |
|---|---|---|---|
| *Plutella xylostella* | 50 | 0 | 100 |
| *Spodoptera litura* | 500 | 0 | — |
| | 50 | 0 | 4 |
| Adoxophyes sp. | 50 | 6 | 47 |
| *Spodoptera exigua* | 50 | 10 | 3 |
| *Bombyx mori* | 50 | 0 | 70 |

*Number of samples = 50 larvae in the first to third instar.

Test 3. Electrophoresis of insecticidal proteins accumulating in the cells of *japonensis* strain and *B.t.* Buibui: *B.t.* Buibui produces, in the cells, spherical crystalline proteins as does *japonensis* strain (FIGS. 5 and 6). The crystalline proteins were isolated from the culture medium by a standard method (Goodman, N. S., R. J. Gottfried, M. J. Rogoff [1987] *J. Bacteriol.* 34:485). After purification, the proteins were dissolved in a 0.4N alkali solution, and analyzed through sodium dodecyl sulfate polyacrylamide gel electrophoresis (SDS-PAGE). As shown in FIG. 7, *japonensis* strain has a main band at about 76 kDa, and a different band at 52 kDa. *B.t.* Buibui has a main band at about 130 kDa, and different bands at 52 kDa and 45 kDa. These electrophoresis patterns clearly show that the two types of crystalline proteins have different ingredients.

Test 4. Difference in adoptivity in culture media between *japonensis* strain and *B.t.* Buibui: As shown in Table 3, *japonensis* strain adopts glucose, salicin, and maltose, does not adopt mannose, and adopts cellobiose to a certain degree. *B.t.* Buibui can adopt all of these substances.

These features show that, taxonomically, *B.t.* Buibui is classified by serotype as *japonensis* strain, but clearly is a cell different from *japonensis* strain.

TABLE 3

| Sugars | japonensis | Buibui |
|---|---|---|
| glucose | ++ | ++ |
| D-(+)-xylose | − | − |
| D-(+)-arabinose | − | − |
| mannitol | − | − |
| galactose | − | − |
| mannose | − | ++ |
| salicin | ++ | ++ |
| sucrose | +− | +− |
| D-(+)-cellobiose | +− | ++ |
| maltose | ++ | ++ |

TABLE 3-continued

| Sugars | japonensis | Buibui |
|---|---|---|
| lactose | − | − |
| acetoin | + | + |
| urease | ++ | ++ |

++ = adopt very well; + = adopt well; +− = adopt; − = do not adopt

B.t. Buibui can be cultured using standard art media and fermentation techniques. Specific examples of fermentation media and techniques are provided in the examples which follow. Upon completion of the fermentation cycle, the bacteria can be harvested by first separating the B.t. spores and crystals from the fermentation broth by means well known in the art. The recovered B.t. spores and crystals can be formulated into a wettable powder, liquid concentrate, granules, or other formulations by the addition of surfactants, dispersants, inert carriers and other components to facilitate handling and application for particular target pests. These formulation and application procedures are all well known in the art.

DNA containing the toxin gene from B.t. Buibui can be purified from E. coli KBR9207 by standard procedures well known in the art. The toxin gene can be excised from the plasmid DNA by restriction enzyme digestion. This subject invention pertains not only to the specific DNA sequence shown in SEQ ID NO. 1, but also to variations of this sequence which code for an amino acid sequence having activity against coleopteran characteristics of the toxin produced by B.t. Buibui. These DNA sequences would be expected to have a high degree of homology and, for example, would be expected to hybridize with each other and/or common probes or primers under high stringency conditions. Similarly, the subject invention pertains not only to the protein having the amino acid sequence shown in SEQ ID NO. 2, but also to equivalent toxins having the same or similar biological activity of the toxin shown in SEQ ID NO. 2. These equivalent toxins may have amino acid homology with the toxin disclosed and claimed herein. This amino acid homology will typically be greater than 50%, preferably be greater than 75%, and most preferably be greater than 90%. The amino acid homology will be highest in certain critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 4 provides a listing of examples of amino acids belonging to each class.

TABLE 4

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

The genes and toxins according to the subject invention include not only the full length sequences disclosed herein but also fragments of these sequences, or fusion proteins, which retain the characteristic coleopteran activity of the toxins specifically exemplified herein.

It should be apparent to a person skilled in this art that genes coding for coleopteran-active toxins can be identified and obtained through several means. The specific genes may be obtained from a culture depository as disclosed herein. Alternatively, these genes, or portions thereof, may be constructed synthetically, for example, by use of a gene machine. Variations of these genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which code for active fragments may be obtained using a variety of other restriction enzymes. Proteases may be used to directly obtain active fragments of these toxins.

DNA of the subject invention, which codes for coleopteran-active toxin, can be introduced into a wide variety of microbial and plant hosts. Expression of the DNA results, directly or indirectly, in the production and maintenance of the pesticide. With suitable hosts, e.g., Pseudomonas, the microbes can be applied to the situs of coleopteran insects where they will proliferate and be ingested by the insects. The result is a control of the unwanted insects. Alternatively, a microbe hosting the toxin-coding DNA can be treated under conditions that prolong the activity of the toxin produced in the cell. The treated cell then can be applied to the environment of target pest(s). The resulting product retains the toxicity of the B.t. toxin.

Where the B.t. toxin-coding DNA is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and phytosphere yeast species such as *Rhodotorula rubra, R. glutinis, R. marina, R. aurantiaca, Cryptococcus albidus, C. diffluens, C laurentii, Saccharomyces rosei, S. pretoriensis, S. cerevisiae, Sporobolomyces roseus, S. odorus, Kluyveromyces veronae,* and *Aureobasidium pollulans*. Of particular interest are the pigmented microorganisms.

A wide variety of ways are available for introducing the B.t. DNA expressing the toxin into the microorganism host under conditions which allow for stable maintenance and expression of the gene. These methods are well known and easily practiced by those skilled in this art. The transformants can be isolated in accordance with conventional ways, usually employing a selection technique, which allows for selection of the desired organism as against unmodified organisms or transferring organisms, when present. The transformants then can be tested for pesticidal activity.

The B.t. cells can be treated prior to formulation to prolong the pesticidal activity when the cells are applied to the environment of a target pest. Such treatment can be by chemical or physical means, or by a combination of chemical and/or physical means, so long as the technique does not deleteriously affect the properties of the pesticide, nor diminish the cellular capability in protecting the pesticide. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as formaldehyde and glutaraldehyde; anti-infectives, such as zephiran chloride; alcohols, such as isopropyl and ethanol; various histologic fixatives, such as Bouin's fixative and Helly's fixative (See: Humason, Gretchen. L, *Animal Tissue Techniques,* W. H. Freeman and Company, 1967); or a combination of physical (heat) and chemical agents that prolong the activity of the toxin produced in the cell when the cell is applied to the environment of the target pest(s). Examples of physical means are short wavelength radiation such as gamma-radiation and X-radiation, freezing, UV irradiation, lyophilization, and the like. The cell will usually be intact and be substantially in the proliferative form when treated, rather than in a spore form, although in some instances spores may be employed.

The treated cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the B.t. insecticidal gene may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The B.t. or transformed cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

Another approach that can be taken is to incorporate the spores and crystals of B.t. Buibui into bait granules containing an attractant and applying these granules to the soil for control of soil-inhabiting Coleoptera. Formulated B.t. Buibui can also be applied as a seed-coating or root treatment or total plant treatment.

The pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the coleopteran pest(s), e.g., plants, soil or water, by spraying, dusting, sprinkling, or the like.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing B.t. Buibui

A subculture of B.t. Buibui can be used to inoculate the following medium, a peptone, glucose, salts medium.

Bacto Peptone 7.5 g/l
Glucose 1.0 g/l
$KH_2PO_4$ 3.4 g/l
$K_2HPO_4$ 4.35 g/l
Salt Solution 5.0 ml/l
$CaCl_2$ Solution 5.0 ml/l
Salts Solution (100 ml)
  $MgSO_4 \cdot 7H_2O$ 2.46 g
  $MnSO_4 \cdot H_2O$ 0.04 g
  $ZnSO_4 \cdot 7H_2O$ 0.28 g
  $FeSO_4 \cdot 7H_2O$ 0.40 g
$CaCl_2$ Solution (100 ml)
  $CaCl_2 \cdot 2H_2O$ 3.66 g
pH 7.2

The salts solution and $CaCl_2$ solution are filter-sterilized and added to the autoclaved and cooked broth at the time of inoculation. Flasks are incubated at 30 C. on a rotary shaker at 200 rpm for 64 hr.

The above procedure can be readily scaled up to large fermentors by procedures well known in the art.

The *B.t.* spores and crystals, obtained in the above fermentation, can be isolated by procedures well known in the art. A frequently-used procedure is to subject the harvested fermentation broth to separation techniques, e.g., centrifugation.

EXAMPLE 2

Further Methods for Culturing *B.t.* Buibui

*B.t.* Buibui easily grows in culture media commonly used for culturing bacteria, such as L-broth, nutrient broth, and the like, and produces spores and crystalline proteins. Inventors have reviewed highly productive media for culturing *B.t.* Buibui to produce insecticidal ingredients including the crystalline proteins.

First, $3.3 \times 10^5$ spores were inoculated into an agar medium on a 9 cm petri dish. The crystalline proteins produced in 10 days were observed through a microscope. A medium having $MnSO_4$ (10-#M) added to L-broth was the most productive, the order of productivity being as follows:

L-broth+$MnSO_4$>spizizen+amino acid>L-broth>PGSM>spizizen+ casamino acid+vitamin>spizizen+casamino acid>NYS>NYS+ casamino acid.

The respective media have the following compositions:

L-broth: 10 g of tryptose, 5 g of yeast extract, and 5 g of table salt, all per 1 liter, and pH=7.18 to 7.2.

Spizizen: 14 g of potassium 1-hydrogen phosphate ($K_2H$), 6 g of potassium 2-hydrogen phosphate ($KH_2PO_4$), 2 g of ammonium sulfate, 0.2 g of magnesium sulfate, 1 g of sodium citrate, and 5 g of glucose, all per 1 liter, and pH=7.0.

NYS: 1.25 g of nutrient broth, 1.25 g of tryptton, 0.5 g of yeast extract, 10.3 g of calcium chloride, 20.35 g of magnesium chloride, 1.0 g of manganese chloride, 0.02 g of iron sulfate, and 0.02 g of zinc sulfate, all per 1 liter, and pH=7.2.

NYS+casamino acid: 2.0 g of casamino acid added to the above NYS medium, and pH=7.2.

Next, in preparing an insecticide using the insecticidal crystalline proteins produced by the subject cells and effective on coleopterous larvae, the microorganisms according to the invention are cultured in the various media noted above, or in solid media such as fish meal, soy bean powder and the like, or in wastes from starch or sugar processing such as corn syrup and corn steep. The cells cultured by the various methods as above are condensed into creamy form. This is appropriately diluted with water or the like to be sprayed as an insecticide. An antiseptic, extender, and the like, may be mixed into the creamy substance by a usual method. The creamy substance may subsequently be reduced to powder form by means of a spray dryer.

The above method uses the cells themselves which produce the toxin proteins. However, only the crystalline proteins may be used after culturing the cells until autolysis. The product thus obtained is used as a viable microbe cell preparation since the cells produce spores. The toxin proteins produced by these cells do not show toxicity to *Bombyx mori*. Thus, use of the viable microbe cell preparation having spores is not destructive at all to silk culture. Further, the spores may be killed with a suitable compound for use as a killed microbe cell preparation.

A method of spraying the above preparation will be described next. Coleopterous larva to be killed usually live in soil. Thus, the insecticide having the subject cells as an effective ingredient may be sprayed into soil, or may be scattered together with leaf mold which is immediately followed by a mixing operation with a cultivator or the like. A suspension of the above insecticide may be injected directly into soil by using an automatic or manual injector or the like. For this purpose, a fully automatic injector may be installed on a cultivator.

EXAMPLE 3

Insecticidal Activity of *B.t.* Buibui with Respect to *Anomala cuprea* Hope, a Coleopteran As noted hereinabove, Buibui strain shows a very high degree of insecticidal activity not reported heretofore, with respect to *Anomala cuprea* Hope. The insecticidal activity of *B.t.* Buibui was examined using larvae of *Anomala cuprea* Hope in the first to third instars.

The activity was evaluated as follows: 2 ml of water containing insecticidal ingredients was added to 2 g of dry leaf mold. The mixture was placed in a plastic cup. The larvae were then placed one after another and kept therein for a predetermined time.

The insecticidal ingredients included a culture solution of Buibui strain (i.e., a solution containing Buibui strain cells) and crystalline toxin proteins isolated from the culture solution and purified. The insecticidal activity of each ingredient was examined. It is to be noted that the death rate is the number of dead larvae divided by the total number of larvae.

Figure 8:
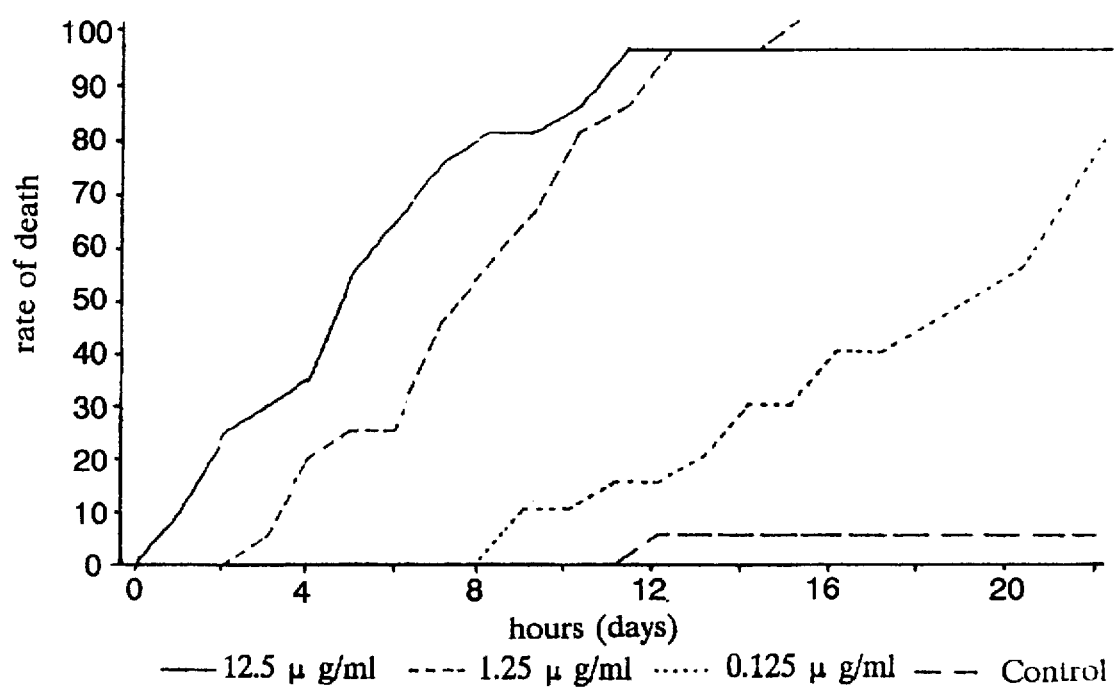
FIG. 8 is a graph showing time-dependent death curves of larvae of *Anomala cuprea* Hope. —12.5 µg/ml; —1.25 µg/ml; . . . 0.125 µg/ml; — —control.

FIG. 8 shows how the death rate varies with lapse of time depending on quantity of the insecticidal ingredient (toxin) comprising the culture solution. It will bee seen that 100% death rate is obtained with a low toxin dosage of 0.125 µg/ml and with a high dosage of 12.5 µg/ml. It has been found, however, that twice the time is taken before all the larvae were killed in the case of a low concentration.

The term "control" in FIG. 8 signifies variations occurring when only water containing no toxin is applied.

As shown in Table 5, the insecticidal ingredient comprising the crystalline proteins isolated and purified, showed insecticidal activity on its own. No insecticidal activity was detected with crystals 0.1 µg/ml. However, 100% death rate was obtained, though slowly, when the culture solution containing 130 kDa proteins in 1 µg/ml was applied to *Anomala cuprea* Hope as noted hereinabove (FIG. 8). This is considered due to the fact that spores present in the cells cooperate with the crystalline proteins in *Anomala cuprea* Hope to show the high degree of activity, and not that activity is lost due to denaturation of the proteins in the course of purification of the crystalline proteins. Thus, the insecticide may contain the cells.

TABLE 5

Insecticidal activities of culture solution and crystalline proteins of Buibui strain with respect to *Anomala cuprea* Hope

| Toxin dosage | Death rates* (%) | | |
| --- | --- | --- | --- |
| (µg 130 kDa protein/ml) | 7th day | 14th day | 21st day |
| Culture solution | | | |
| 10 | 60 | 100 | |
| 1 | 40 | 95 | 100 |

TABLE 5-continued

Insecticidal activities of culture solution and crystalline proteins of Buibui strain with respect to *Anomala cuprea* Hope

| Toxin dosage | Death rates* (%) | | |
|---|---|---|---|
| (μg 130 kDa protein/ml) | 7th day | 14th day | 21st day |
| Crystalline proteins | | | |
| 10 | 50 | 100 | |
| 1 | 0 | 10 | 20 |
| 0.1 | 0 | 0 | 0 |

*Number of samples = 20 larvae in the first instar. The cells were cultured in NYS.

EXAMPLE 4

Insecticidal Effects of *B.t.* Buibui on Larvae of Other Coleopterans

As shown in Table 6, Buibui strain showed a higher degree of insecticidal activity with respect also to *Anomala rufocuprea* Motschulsky, *Anomala schoenfeldti* Ohaus, apart from *Anomala cuprea* Hope. Thus, Buibui strain is expected to show insecticidal effect on larvae of several other *Minela splendens*. Thus, the insecticide is not limited in application to these three types of coleopterans.

TABLE 6

Insecticidal activities of crystalline proteins produced by Buibui strain with respect to *Anomala rufocuprea* Motschulsky and *Anomala schoenfeldti* Ohaus

| Insects | Toxin dosage *μg 130 kDa protein/ml) | Death rates | | | | | |
|---|---|---|---|---|---|---|---|
| | | 4 | 7 | 10 | 14 | 18 | 21st days |
| *Anomala schoenfeldti* Ohaus | 50 | 0 | 10 | 20 | 30 | 60 | 90 |
| *Anomala rufocuprea* Motschulsky | 50 | 0 | 10 | 20 | 30 | 60 | 100 |
| Larvae in 3rd instar of *Anomala rufocuprea* Motschulsky | 50 | 0 | 10 | 30 | 30 | 70 | 90 |
| Control | 0 | 0 | 0 | 0 | 0 | 0 | 10 |

The insects other than the larvae in the third instar of *Anomala rufocuprea* Motschulsky were all larvae in the first instar. The crystals were purified from cells cultured in NYS. The number of samples was 10.

The term "control" above shows results obtained when only water containing no toxin is applied (in a comparative test).

EXAMPLE 5

Insecticidal Effects on Other Coleopterans

The insecticidal activity of Buibui strain was examined, using larvae in the first instar of *Anomala albopilosa*, larvae in the first instar of *Anomala daimiana*, larvae in the first instar of *Minela splendens*, larvae in the first instar of *Popillia japonica*, and larvae in the second instar of *Blitopertha orientalis*. The samples were young larvae hatched from eggs of adults collected outdoors and temporarily bred in a commercially available leaf mold.

The testing method was as follows: 1 gram of leaf mold dried and sterilized in a dry oven at 160 C. for 60 minutes was weighed with a cup having a lid and a capacity of about 30 ml. Buibui culture in a predetermined concentration was mixed into the cup and sufficiently stirred, and then one larva was placed therein. A plurality of such mixtures were prepared, and bred in a thermostatic chamber at 25 C. The death rate was checked on the 7th, 14th, and 21st days to determine potency of Buibui. The results are shown in Table 7.

TABLE 7

| Larvae | Toxin dosage 130 kDa protein μg/g leaf mold | Death rates (%) | | |
|---|---|---|---|---|
| | | 7th | 14th | 21st day |
| *Anomala albopilosa* in first instar | 50 | 100 | 100 | 100 |
| | 0.1 | 0 | 0 | 0 |
| *Anomala daimiana* in first instar | 50 | 0 | 50 | 70 |
| | 0.1 | 25 | 25 | 25 |
| *Minela splendens* in first instar | 50 | 100 | 100 | 100 |
| | 0.1 | 0 | 100 | 100 |
| *Popillia japonica* in first instar | 50 | 100 | 100 | 100 |
| *Blitopertha orientalis* in second instar | 50 | 100 | 100 | 100 |

The number of samples were 8 and 5 for *Anomala daimiana* and *Blitopertha orientalis*, respectively, and 10 for all the others.

As noted above, Buibui strain showed insecticidal activity with respect to *Anomala albopilosa*, *Anomala daimiana*, *Minela splendens*, *Popillia japonica*, and *Blitopertha orientalis*. In the case of *Anomala daimiana*, the death rate was 70% after 21 days, which is lower than the rates of the other insects. However, no increase in the weight was observed, and it was obvious that the larvae of *Anomala daimiana* were to die in due course. Thus, although some delays were observed, the cessation of food intake is considered equivalent to death. Particularly important is the insecticidal property to kill what are known as Japanese beetles, which are causing a serious problem in the United States.

Having determined the activity with respect to several coleopterans, the fact that the activity with respect to Popillia, Minela, and Blitopertha species as well as Anomala species suggests that the subject cells are not limited in application to those insects listed in Tables 6 and 7 but are applicable to a wide variety of coleopteran pests.

EXAMPLE 6

Activity of Beta-Exotoxin

Some of Bacillus strain cells excrete into culture media beta-exotoxin, which is a nucleotide derivative. It has an insecticidal effect similar to that of toxin proteins. Beta-exotoxin shows teratogenic action with respect to larvae of house flies, which provides a basis for evaluating the activity of beta-exotoxin. However, as shown in Table 8, when a supernatant of culture was prepared from a medium of Buibui strain by a usual method and applied to house flies, Buibui strain showed no teratogenesis with their pupation rate and eclosion rate remaining unaffected. When the above treating medium of Buibui strain was applied to *Anomala cuprea* Hope, its larvae remained alive after lapse of 14 days as shown in Table 9. The results of this test show that the insecticidal effect of Buibui strain on *Anomala cuprea* Hope does not depend on beta-exotoxin.

That is, beta-exotoxin does not exist to the extent of influencing the test results.

TABLE 8

Effect of beta-exotoxin in Buibui strain culture medium on house flies

|  |  | pupation rate (%) | eclosion rate (%) |
|---|---|---|---|
| Buibui culture |  | 86.7 | 80 |
| Standard beta-exotoxin | 2 ppm | 90 | 0 |
|  | 0.2 ppm | 100 | 0 |
| Distilled water |  | 93.3 | 93.3 |

TABLE 9

Insecticidal effect of Buibui strain culture medium* on *Anomala cuprea* Hope

|  | Death rates (%) | |
|---|---|---|
|  | 7th day | 14th day |
| Buibui culture* | 0 | 0 |
| Distilled water | 0 | 0 |

*The above Buibui medium refers to the medium remaining after strain cells are removed from the medium by centrifugal separation.

EXAMPLE 7

Insertion of Toxin Gene Into Plants

One aspect of the subject invention is the transformation of plants with genes coding for a coleopteran-active toxin. The transformed plants are resistant to attack by coleopterans.

Genes coding for coleopteran-active toxins, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence coding for the *B.t.* toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (1985) In: *The Binary Plant Vector System*, Offset-durkkerij Kanters B. V., Alblasserdam, Chapter 5; Fraley et al., *Crit. Rev. Plant Sci.* 4:1–46; and An et al. (1985) *EMBO J.* 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, or electroporation as well as other possible methods. If agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in agrobacteria. The intermediate vector can be transferred into *Agrobacterium tumefaciens* by means of a helper plasmid (conjugation). Binary vectors can replicate themselves both in *E. coli* and in agrobacteria. They comprise a selection marker gene and a linker or polylinker which are framed by the right and left T-DNA border regions. They can be transformed directly into agrobacteria (Holsters et al. [1978] *Mol. Gen. Genet.* 163:181–187). The agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

EXAMPLE 8

Cloning of Novel *B. thuringiensis* Genes Into Insect Viruses

A number of viruses are known to infect insects. These viruses include, for example, baculoviruses and entomopoxviruses. In one embodiment of the subject invention, antactive genes, as described herein, can be placed with the genome of the insect virus, thus enhancing the pathogenicity of the virus. Methods for constructing insect viruses which comprise *B.t.* toxin genes are well known and readily practiced by those skilled in the art. These procedures are described, for example, in Merryweather et al. (Merryweather, A. T., U. Weyer, M. P. G. Harris, M. Hirst, T. Booth, R. D. Possee (1990) *J. Gen. Virol.* 71:1535–1544)

and Martens et al. (Martens, J. W. M., G. Honee, D. Zuidema, J. W. M. van Lent, B. Visser, J. M. Vlak (1990) *Appl. Environmental Microbiol.* 56(9):2764–2770).

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A recombinant or substantially pure coleopteran-active toxin, wherein said toxin has an amino acid sequence that is at least 75% the same as the amino acid sequence of SEQ ID NO. 2, or a coleopteran-active part thereof.

2. The toxin, according to claim 1, which comprises the amino acid sequence of SEQ ID NO. 2 or a coleopteran-active part thereof.

* * * * *

UNITED STATES PATENT AND TRADEMARK OFFICE
CERTIFICATE OF CORRECTION

PATENT NO. : 5,747,450
DATED : May 5, 1998
INVENTOR(S) : Ohba, et. al.

It is certified that error appears in the above-indentified patent and that said Letters Patent is hereby corrected as shown below:

Column 13, line 35, Table 6 subheading: "*$\mu$g 130 kDa" should read --($\mu$g 130 kDa--.

Signed and Sealed this

Twenty-fifth Day of August, 1998

Attest:

BRUCE LEHMAN

*Attesting Officer*     *Commissioner of Patents and Trademarks*